US009612195B1

(12) United States Patent
Friedman (10) Patent No.: US 9,612,195 B1
(45) Date of Patent: Apr. 4, 2017

(54) GAS DETECTOR AND METHOD FOR MONITORING GAS IN A CONFINED SPACE

(71) Applicant: Bert Friedman, Chicago, IL (US)

(72) Inventor: Bert Friedman, Chicago, IL (US)

(73) Assignee: Bert Friedman, Chicago, IL (US)

( * ) Notice: Subject to any disclaimer, the term of this patent is extended or adjusted under 35 U.S.C. 154(b) by 0 days.

(21) Appl. No.: 15/010,948

(22) Filed: Jan. 29, 2016

Related U.S. Application Data

(60) Provisional application No. 62/254,001, filed on Nov. 11, 2015.

(51) Int. Cl.
| G01N 21/00 | (2006.01) |
| G01N 21/3504 | (2014.01) |
| G01N 33/00 | (2006.01) |
| G08B 21/14 | (2006.01) |
| G08B 21/16 | (2006.01) |

(52) U.S. Cl.
CPC ....... G01N 21/3504 (2013.01); G01N 33/004 (2013.01); G08B 21/14 (2013.01); G08B 21/16 (2013.01)

(58) Field of Classification Search
CPC ............. G01N 21/359; G01N 33/0057; G01N 24/084; G01N 21/35
See application file for complete search history.

(56) References Cited

U.S. PATENT DOCUMENTS

| 5,568,121 A | 10/1996 | Lamensdorf |
| 6,469,303 B1 | 10/2002 | Sun et al. |
| 7,233,781 B2 | 6/2007 | Hunter et al. |
| 7,258,773 B2 | 8/2007 | Zhou et al. |
| 7,688,198 B2 | 3/2010 | Amidi |
| 7,848,732 B2 | 12/2010 | Thomas |
| 7,959,777 B2 | 6/2011 | Scheffler |
| 8,330,605 B2 | 12/2012 | Johnson, Jr. et al. |
| 8,503,943 B2 | 8/2013 | Spanhake |

(Continued)

FOREIGN PATENT DOCUMENTS

| WO | 2013072700 A1 | 5/2013 |
| WO | 2015019067 A1 | 2/2015 |
| WO | 2015166265 A1 | 11/2015 |

OTHER PUBLICATIONS

Rae Systems, Datasheet—QRAE 3 Wireless 4-Gas Monitor, Sep. 10, 2015, DS-1095-06, accessed online at <http://www.raesystems.com/customer-care/resource-center/qrae-3-datasheet>.

(Continued)

*Primary Examiner* — Kiho Kim
(74) *Attorney, Agent, or Firm* — Flener IP Law, LLC; Zareefa B. Flener; Michal A. Gawlik (57) ABSTRACT

A gas detector for use in a confined space is described. The gas detector includes a plurality of gas sensors, a location module, at least one geometry sensor, a communication module, and a processing unit. The processing unit receives gas data from the plurality of gas sensors, location data from the location module, and geometry data from the at least one geometry sensor. The processing unit further calculates space data based on at least one of the gas data and the geometry data. The communication module transmits a signal based on at least two selected from the group consisting of the gas data, the location data, the geometry data, and the space data.

20 Claims, 6 Drawing Sheets

(56) References Cited

U.S. PATENT DOCUMENTS

| | | | |
|---|---|---|---|
| 8,779,921 B1* | 7/2014 | Curtiss | G08B 25/009 340/506 |
| 8,818,713 B2 | 8/2014 | Kumar et al. | |
| 2007/0272553 A1* | 11/2007 | Gambert | G01N 27/404 204/431 |
| 2008/0122641 A1* | 5/2008 | Amidi | G01N 33/0075 340/632 |
| 2008/0229500 A1* | 9/2008 | Lin | A47C 15/002 5/417 |
| 2010/0063652 A1* | 3/2010 | Anderson | A61B 5/02438 701/2 |
| 2010/0078560 A1 | 4/2010 | Basham | |
| 2011/0161885 A1 | 6/2011 | Gonia et al. | |
| 2012/0212347 A1 | 8/2012 | Boone | |
| 2012/0297868 A1 | 11/2012 | Elkins | |
| 2012/0315705 A1* | 12/2012 | Allyn | G01N 33/0075 436/159 |
| 2013/0278412 A1 | 10/2013 | Kelly et al. | |
| 2013/0295538 A1* | 11/2013 | Ambrose | G09B 9/00 434/218 |
| 2014/0011286 A1 | 1/2014 | Potyrailo et al. | |
| 2014/0238100 A1 | 8/2014 | Londergan et al. | |
| 2014/0347181 A1 | 11/2014 | Luna et al. | |
| 2015/0075256 A1 | 3/2015 | Basham et al. | |
| 2015/0112883 A1 | 4/2015 | Orduna et al. | |
| 2015/0115746 A1 | 4/2015 | Rosso | |

OTHER PUBLICATIONS

Honeywell, Brochure—ConneXt Loneworker Solution, Nov. 2, 2015, 151102AMBR-1-EN ConneXt Loneworker Brochure_NA, accessed online at <http://www.honeywellanalytics.com/en/products/ConneXt-Loneworker>.

Honeywell, Product Specifications—ConneXt Loneworker Solution, Oct. 31, 2015, 151031AMSS-1-EN ConneXt Loneworker Spec Sheet_NA, accessed online at <http://www.honeywellanalytics.com/en/products/ConneXt-Loneworker>.

BW Technologies, Datasheet—GasAlert MicroClip, Jul. 18, 2015, 20150718-02-US-EN, accessed online at <http://www.honeywellanalytics.com/en/products/GasAlertMicroClip-Series>.

* cited by examiner

GAS DETECTOR AND METHOD FOR MONITORING GAS IN A CONFINED SPACE

TECHNICAL FIELD

The present invention relates to a gas detector and method for monitoring gas in a confined space. Specifically, the present invention relates to a gas detector and method which complies with Occupational Safety and Health Administration ("OSHA") regulations requiring workers entering confined spaces with possible hazardous gases to wear and operate a gas detector during the course of their job.

SUMMARY

Many different environments have to deal with the presence of toxic or hazardous materials. For example, chemical production facilities often use or produce hazardous gases. As another example, mines often have hazardous gases that build up within the mines. In these or other environments, it is often necessary or desirable to allow workers to determine the level of hazardous materials in these environments.

Gas detectors are configured to provide accurate data on hazardous (i.e., toxic) gas exposure in accordance with OSHA regulations for confined spaces. Gas detectors typically involve a diverse range of sensor technologies and features.

Gas detectors are designed to detect oxygen, carbon monoxide, hydrogen sulfide, and combustible (i.e., lower explosive limit ["LEL"]) gas levels. If the measured gas levels exceed a threshold, an alarm is typically displayed and/or sounded to warn the workers of the excessive gases.

Although, various gas detectors are available to assist workers in confined spaces as noted above, such systems are not completely satisfactory. For the improved safety of workers, additional information, such as location (e.g., Global Positioning System ["GPS"]) data and geometry data, may be collected. As such, it is useful for gas detectors to receive location data and geometry data from modules and/or sensors instead of separate devices (e.g., routers). In addition, such data can be used for purposes of calculating additional data about a confined space.

The present invention relates to a gas detector for use in a confined space. The gas detector includes a plurality of gas sensors, a location module, at least one geometry sensor, a communication module, and a processing unit. The plurality of gas sensors measure one or more hazardous material. The processing unit receives gas data from the plurality of gas sensors, location data from the location module, and geometry data from the at least one geometry sensor. The processing unit transmits a signal based on the gas data and the location data using the communication module.

The present invention also relates to a gas detector for use in a confined space. The gas detector includes a plurality of gas sensors, a location module, at least one geometry sensor, a communication module, and a processing unit. The plurality of gas sensors measure one or more hazardous material. The processing unit receives gas data from the plurality of gas sensors, receives location data from the location module, and receives geometry data from the at least one geometry sensor. The processing unit calculates space data based on at least one of the gas data and the geometry data and transmits a signal based on at least two selected from the group consisting of the gas data, the geometry data, and the space data using the communication module.

The present invention further relates to a method for monitoring gas in a confined space. The method includes the steps of receiving, at a processing unit, gas data from a plurality of gas sensors, location data from a location module, and geometry data from at least one geometry sensor. The method further calculates, at the processing unit, space data based on the gas data and the geometry data. A signal based on at least two selected from the group consisting of the gas data, the location data, the geometry data, and the space data is transmitted using the communication module.

The present invention further relates to a gas detector wherein the plurality of gas sensors consists of a lower explosive limit ("LEL") sensor, an oxygen sensor, a first toxic sensor, and a second toxic sensor; the at least one geometry sensor consists of a laser and a level, and the geometry data consists of a distance. In other embodiments, the communication module consists of a Bluetooth chip and/or a Global System for Mobile Communications ("GSM") chip, and the signal is transmitted to an external device and/or a remote server. In yet other embodiments, the gas detector further includes a memory module (e.g., a removable SD card) operable to store the gas data, the location, the geometry data, and the space data.

Other advantages and features of the disclosure will become apparent upon review of the detailed description and accompanying drawings.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Accordingly, the detailed discussion herein of one or more embodiments is not intended, nor is to be construed, to limit the metes and bounds of the patent protection afforded the present invention, in which the scope of patent protection is intended to be defined by the claims and equivalents thereof. Therefore, embodiments not specifically addressed herein, such as adaptations, variations, modifications, and equivalent arrangements, should be and are considered to be implicitly disclosed by the illustrative embodiments and claims described herein and therefore fall within the scope of the present invention.

Additionally, it is important to note that each term used herein refers to that which a person skilled in the relevant art would understand such term to mean based on the contextual use of such term herein. To the extent that the meaning of a term used herein, as understood by the person skilled in the relevant art based on the contextual use of such term, differs in any way from any particular dictionary definition of such term, it is intended that the meaning of the term as understood by the person skilled in the relevant art should prevail.

Figure 1:
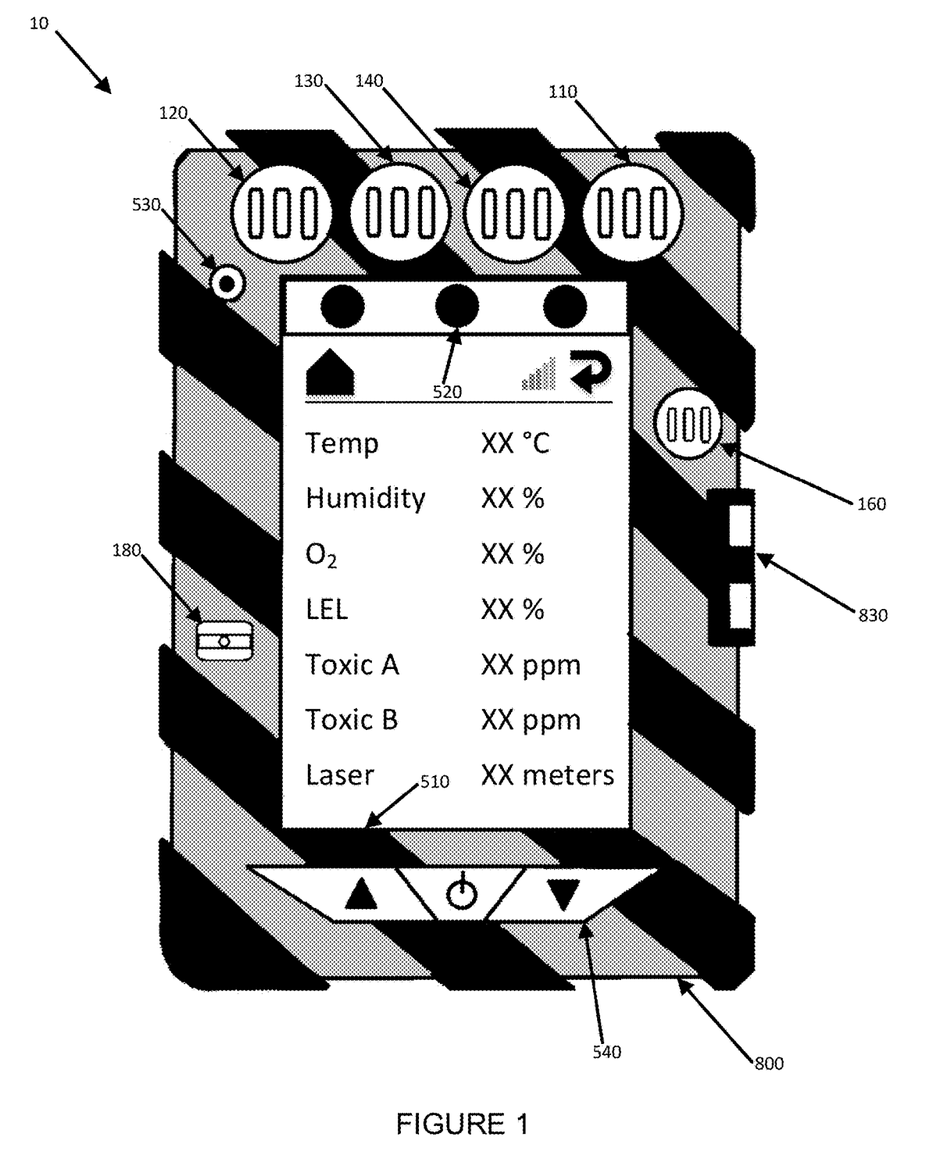
FIG. 1 illustrates an exterior view of a gas detector, in accordance with the principles of the present invention.

FIG. 1 illustrates a gas detector 10 (i.e., gas monitor, portable gas device, multi-gas detector) in accordance with an embodiment of the present invention. The gas detector 10 includes a plurality of sensors, a user interface, and an enclosure 800. The enclosure 800 protects internal components of the gas detector 10 from the environment (more detail in reference to FIG. 6). A clasp 830 allows access to internal (e.g., electronic) components of the gas detector 10. The user interface may include a display 510 (e.g., a liquid crystal display ["LCD"]), a light-emitting diode ("LED") bar 520, an audible speaker (i.e., buzzer, alarm) 530, and a plurality of buttons 540.

In one embodiment, the plurality of sensors of the gas detector 10 includes, but is not limited to, a combustible (i.e., lower explosive limit ["LEL"]) sensor 110, an oxygen sensor 120, a first toxic sensor 130, and a second toxic sensor 140. The LEL sensor 110 detects and measures hazardous gases such as alkanes, for example, but not limited to, methane, ethane, propane; alcohols, for example but not limited to, ethanol, methanol; alkenes, for example, but not limited to, ethylene oxide, propylene oxide, benzene; and other gases, for example, but not limited to, hydrogen, acetone, ammonia, in a confined space. The LEL sensor 110 can use infrared technology or catalytic technology to detect and measure hazardous gases. Infrared ("IR") LEL sensors 110 detect and measure gases based upon the absorption of infrared radiation at specific wavelengths; catalytic LEL sensors 110 detect and measure gases based upon the heat released when upon oxidation.

In some embodiments, the LEL sensor 110 preferably uses IR technology. By using less battery power this embodiment can be more energy efficient, and provide rapid response detection and measurement of hazardous gases. Additionally, the LEL sensor 110 with IR technology uses fewer powders (e.g., silicates), reducing risks of poisoning a user via use of the gas detector 10 and increasing the operating life of the LEL sensor 110 with IR technology compared to catalytic technology. Measurements from the LEL sensor 110 are displayed on the display 510, for example, as a percentage of a volume of gas detected by the LEL sensor 110.

The oxygen (i.e., "$O_2$") sensor 120 of the gas detector 10 detects and measures the oxygen in confined space. In some embodiments, the oxygen sensor 120 preferably uses lead-free components such as, but not limited to, solid polymer electrolytes ["SPE"]). Lead-free oxygen sensors 120 are less likely to leak and have a longer operating life than oxygen sensors 120 with lead components, for example five years compared to two years. Lead-free oxygen sensors 120 are preferred because they reduce the maintenance costs of using the gas detector 10. Measurements from the oxygen sensor 120 are displayed on the display 510, for example, as a percentage of a volume of gas detected by the oxygen sensor 120.

The first toxic sensor 130 and the second toxic sensor 140 provide additional detection and measurement of toxic (i.e., hazardous) gases. In some embodiments, the first toxic sensor 130 is a combined carbon monoxide and hydrogen sulfide (i.e., "$CO/H_2S$") sensor. CO, $H_2S$, $O_2$, and LEL measurements are required for confined space entry per OSHA guidelines. Measurements from the first toxic sensor 130 and the second toxic sensor 140 are displayed on the display 510, for example, as a particle count such as parts per million ["ppm"]. In some embodiments, the second toxic sensor 140 detects and measures such toxins as ammonia, carbon dioxide, hydrogen cyanide, sulfur dioxide, nitric dioxide, volatile organic compounds (i.e., "VOC"). The first toxic sensor 130 and the second toxic sensor 140 can use infrared technology, catalytic technology, or photoionization technology to detect and measure hazardous gases. In other embodiments, the second toxic sensor 140 is a man-down detector that uses motion sensors to detect a sudden inertial change indicative of a user of the gas detector 10 falling and/or passing out.

Referring to FIG. 1, the sensors 110 through the second toxic sensor 140 use diffusion to detect and measure hazardous gases. A diffusion gas detector 110 uses natural diffusion to acquire gas samples for detection and measurement. In other embodiments, the sensors 110 through the second toxic sensor 140 use a sampling pump to detect and measure hazardous gases. A pump gas detector 110 uses an internal pump to acquire gas samples for detection and measurement. A personal skilled in the art would have sufficient knowledge to modify the gas detector 10 of FIG. 1 to use an internal pump for gas sampling.

In some embodiments, the gas detector 10 has additional sensors for measuring the environment of the confined space. For example, the gas detector 10 includes a humidity sensor 160 and a temperature sensor 150 (not shown; more detail in reference to FIG. 2). The humidity sensor 160 measures the relative humidity (i.e., a percentage of water vapor in the environment) of the confined space, providing additional information for the gas detector 10 for more accurate detection and measurement by the LEL sensor 110, oxygen sensor 120, the first toxic sensor 130, and the second toxic sensor 140.

In some embodiments, the gas detector 10 has sensors for measuring the geometry of the confined space. For example, the gas detector 10 includes a level 180 and a laser 170 (not shown; more detail in reference to FIG. 2). The level 180 can use digital components or analog components to measure the orientation (e.g., degrees from horizontal) of the gas detector 10. A digital level 180 uses a liquid sensor and an electrode to measure a deviation from gravity; an analog level 180 uses a tube with a liquid and a bubble of air. The level 180 may be used to improve the accuracy of measurements taken using the laser 170 (more detail in reference to FIG. 5).

The display 510 depicted in FIG. 1 is, for example, a liquid crystal display ("LCD;" monochrome or color), a light-emitting diode ("LED") display, an organic LED ("OLED") display, an electroluminescent display ("ELD"), a surface-conduction electron-emitter display ("SED"), a field emission display ("FED"), a thin-film transistor ("TFT") LCD, etc. The display 510 can be configured to display conditions or data associated with the gas detector 10 in real-time or substantially real-time. For example, the display 510 can be configured to display measurements from the sensors 110 through 140 of the gas detector 10, the status of the gas detector 10, the position of the gas detector 10 based on measurements from the laser 170 and the level 180, for example.

In some embodiments, the display 510 is controlled in conjunction with the LED bar 520 and the audible speaker 530 to provide visual or auditory indications of the conditions inside the confined space and/or the status of the gas detector 10. For example, additional information, such as a warning message, can be displayed on the LED bar 520 and an alarm can be sounded through the audible speaker 530.

The plurality of buttons 540 allows a user to input information into the gas detector 10, make selections on a menu and/or calibrate sensors, for example. In some embodiments, a user can input information through other features as well, including but not limited to, touch-screen displays, a plurality of knobs, dials, switches, buttons.

Figure 2:
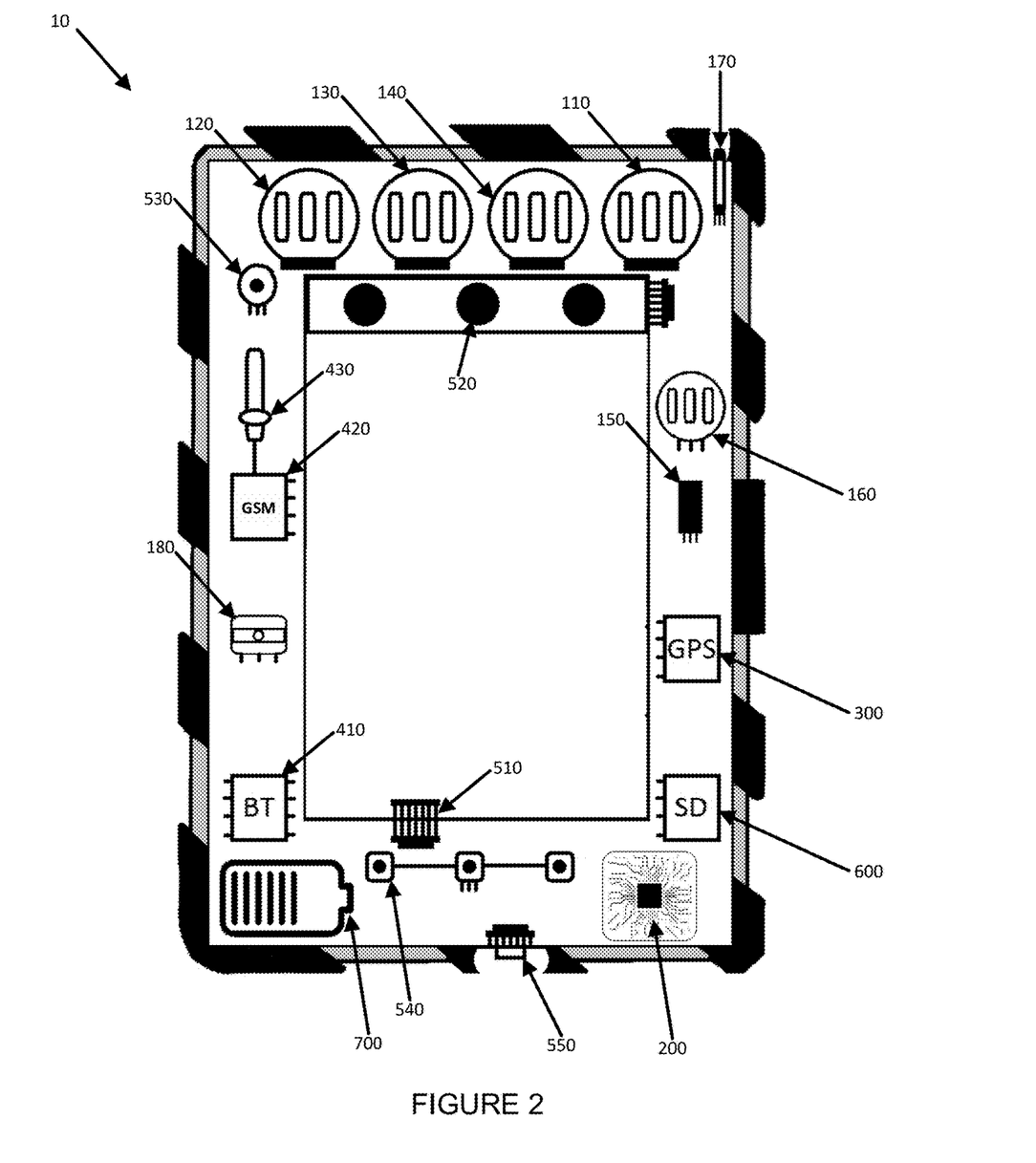
FIG. 2 illustrates an interior view of the gas detector, in accordance with the principles of the present invention.

FIG. 2 illustrates an interior view of the gas detector 10 in accordance with an embodiment of the present invention. As previously disclosed with respect to FIG. 1, the gas detector 10 includes the LEL sensor 110 (e.g., using IR technology), oxygen sensor 120 (e.g., with lead-free components), the first toxic sensor 130 (e.g., a $CO/H_2S$ sensor), and the second toxic sensor 140. In some embodiments, the sensors 110 through 140 and other electronic components of the gas detector 10 are fixed to a printed circuit board ("PCB"). The PCB mechanically supports and electrically connects components of the gas detector 10 using tracks, pads, and other features etched from conductive sheets laminated onto a non-conductive substrate. The PCB may be custom-designed for optimal placement of the sensors 110 through 140 and other components within the gas detector 10.

The gas detector 10 includes a processing unit 200 such as, but not limited to, a controller, processor, multiprocessor, microcontroller, or another suitable programmable device. The processing unit 200 includes a plurality of electrical and electronic components that provide power, operational control, and protection to the components and modules within the gas detector 10. In some embodiments, the processing unit 200 includes, among other things, a control unit, an arithmetic logic unit ("ALU"), and a plurality of registers, and is implemented using a known computer architecture, such as a modified Harvard architecture, a von Neumann architecture, etc. In some embodiments, the processing unit 200 is implemented partially or entirely on a semiconductor, for example, but not limited to, a field-programmable gate array ["FPGA"]) chip, such as a chip developed through a register transfer level ("RTL") design process.

As described with respect to FIG. 1, in some embodiments, the gas detector 10 includes a humidity sensor 160, a level 180 (e.g., analog or digital), a display 510, a LED bar 520, an audible speaker 530, and a plurality of buttons 540. Referring to FIG. 2, in some embodiments, the gas detector 10 further includes a temperature sensor 150. The temperature sensor 150 produces an electrical current (i.e., signal) that is received and interpreted by the processing unit 200 and displays a temperature (e.g., Celsius, Fahrenheit, etc.) of the confined space on the display 510. Additionally, the temperature sensor 150 improves the accuracy of measurements by the sensors 110 through the second toxic sensor 140 and may reduce the number of false alarms by the gas detector 10.

In some embodiments, the gas detector 10 includes a laser 170, for example, but not limited to, a laser tape measure, laser distance meter, laser measurement device). The laser 170 may include a mode-locked laser or any laser with a known frequency. The processing unit 200, in some embodiments, uses a phase-shift method of distance measurement, wherein a subcomponent of the laser (e.g., an optical sensor) compares light reflected back to the laser 170 with light emitted from the laser 170. For example, the equation for calculating a distance ("d") at the processing unit 200 can be, for example, $d=2\pi*\Delta t*\Delta f$, wherein "$\Delta t$" is the time of flight of the light from the laser 170 to a surface of the confined space and "$\Delta f$" is the modulation frequency. In some embodiments, the distance is used to determine or calculate space data for the confined space, such as a volume, surface area, circumference, and/or hypotenuse, by way of example (more detail in reference to FIG. 5).

The gas detector 10 includes a location module 300 capable of identifying a location of the gas detector 10. In some embodiments, the location module 300 is a Global Positioning System ("GPS") receiver. In other embodiments, the location module 300 is a Radio Frequency Identification ("RFID") system.

The location module 300 receives location data using an antenna 430. Based on data received by the antenna 430 from one or more external satellites 30 (see FIG. 3), the location module 300 provides location data to the processing unit 200 regarding latitude, longitude, heading, time, and a GPS quality value. In some embodiments, the location module 300 updates the location information periodically in a predetermined frequency (e.g., approximately every 5 seconds). In some embodiments, if the location module 300 is unable to provide updated location data, the location module 300 uses and maintains the last known location data.

In some embodiments, the location data obtained using the location module 300 such as through a GPS receiver is associated with the gas data for instance from sensors 110 through 140, by the processing unit 200 to pinpoint dangerous areas within a workplace, such as a confined space, or reduce the number of false alarms.

The gas detector 10 includes a memory module 600. The memory module 600 includes, for example, a program storage area and a data storage area. The program storage area and the data storage area may include combinations of different types of memory, such as read-only memory ("ROM"), random access memory ("RAM") (e.g., dynamic RAM ["DRAM"], synchronous DRAM ["SDRAM"], etc.), electrically erasable programmable read-only memory ("EEPROM"), flash memory, a hard disk, an SD card, or other suitable magnetic, optical, physical, or electronic memory devices. The processing unit 200 is connected to the memory module 600 and executes software instructions that are capable of being stored in a RAM of the memory module 600, for example during execution, a ROM of the memory module, 600, for instance on a generally permanent basis, or another non-transitory computer readable medium such as another memory or a disc. Software included in the implementation of the gas detector 10 can be stored in the memory module 600. The software includes, for example, firmware, one or more applications, program data, filters, rules, one or more program modules, and other executable instructions. The processing unit 200 is configured to retrieve from memory and execute, among other things, instructions related to the control processes and methods described herein.

In the embodiment shown in FIG. 2, the memory module 600 is a removable Secure Digital ("SD") card that stores the gas data, the geometry data, and/or the location data. In one embodiment, the memory module 600 stores the gas data, the geometry data, and/or the location data every 5 seconds during normal operation, and stores the data every half second during alarm operation (see FIG. 5). The memory module 600 also logs other information related to operation of the gas detector 10, such as for example, the time span over which data was collected, and/or the time the data was retrieved for instance by an external device.

Figure 4:
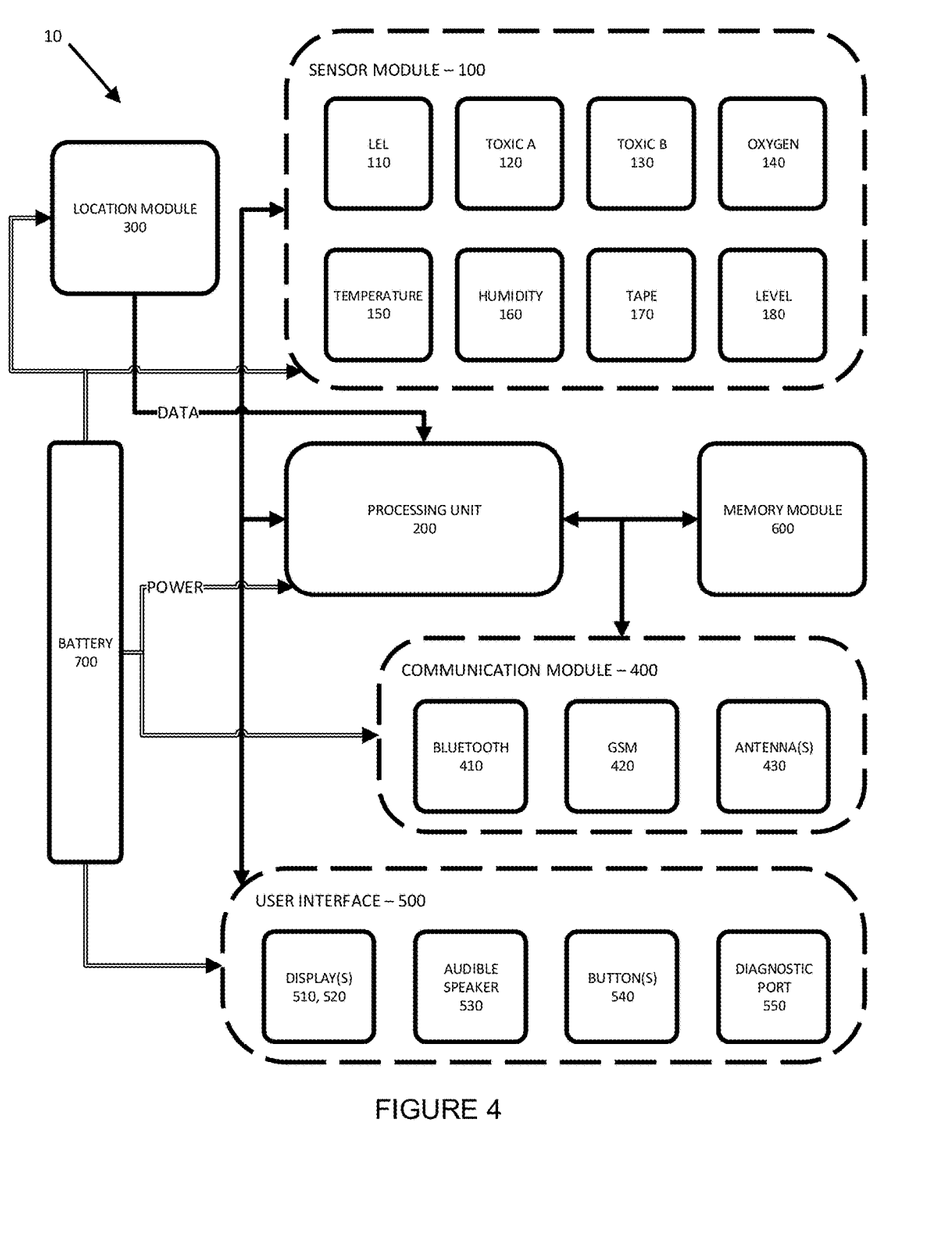
FIG. 4 illustrates a block diagram of the gas detector, in accordance with the principles of the present invention.

The gas detector 10 includes a communication module 400 (see FIG. 4). The communication module 400 may include, but is not limited to, a Bluetooth chip 410, a Global System for Mobile Communication ("GSM") chip 420, and an antenna 430. The antenna 430 could be the same antenna used by the location module 300 or could be a separate antenna. The antenna 430 supports a connection between the gas detector and a network 40 (see FIG. 4). The GSM chip 420 receives a SIM card in order to connect to the GSM (i.e., cellular) network. Using the antenna 430, the GSM chip 420 transmits a signal based on the gas data, the geometry data, and/or the location data received by the processing unit 200. The signal can be transmitted at real-time or stored in the memory module 600 until a connection between the GSM chip 420 and the network 40 is established.

In some embodiments, the communication module 400 also includes one or more encryption chips, modems, or both for communicating with different types of external devices. For example, the communication module 400 may include an Apple® encryption chip and a supported modem, which allows the gas detector 10 to communicate with Apple® devices. The gas detector 10 can similarly include encryption chips and modems for other types of external devices, such as Microsoft® devices, Android® devices, and Linux® devices.

As described above, the gas detector 10 may include a Bluetooth chip 410. The Bluetooth chip 410 can be configured to automatically search and discover other Bluetooth-enabled devices, for example, in a cellular phone). The plurality of buttons 540 can allow a user to control when the gas detector 10 becomes discoverable or searchable. For example, in some embodiments, pressing one of the plurality of buttons 540 for a predetermined period of time (e.g., three seconds) makes the gas detector 10 discoverable or searchable by another Bluetooth-enabled device. Also, if the gas detector 10 is operating in a sleep mode thereby conserving battery power by reducing usage of the Bluetooth chip 410, pressing the button 540 wakes up the processing unit 200 and enables communication via the Bluetooth chip 410. In some embodiments, the gas detector 10 is also configured to automatically become discoverable or searchable via Bluetooth for a predefined period of time after the gas detector 10 is powered or reset.

When the gas detector 10 is discoverable via Bluetooth, an external device 50 (see FIG. 3; e.g., a cellular device) can search for, discover, and couple to the gas detector 10. Once the gas detector 10 and the external device 50 are properly coupled, the display 510 of the gas detector 10 can indicate a status of the connection or coupling. After the external device 50 and the gas detector 10 are coupled, the device 50 and the detector 10 can exchange information. For example, as noted above, the gas detector 10 can transmit the gas data, the geometry data, and/or the location data. In other embodiments, Near Field Communication ("NFC") or infrared ("IR") technology is used to transmit the gas data, the geometry data, and/or the location data. It should be understood that even when the Bluetooth chip 410 is transmitting a signal based on the data to the external device 50, the gas detector 10 continues to monitor and record new data from the sensors 110 through 140 and other sensors and modules, such as, but not limited to, the location module 300, the laser 170, or the lever 180.

Referring to FIG. 2, the gas detector 10 includes a battery 700 such as, for example, a Lithium-ion battery (e.g., a 4-cell rechargeable battery providing 3.6 Volts). The battery 700 provides power to all electronic components of the gas detector 10, such as the sensors 110 through 140, the location module 300, the communication module 400, and additional sensors and modules. In some embodiments, the battery 700 may be a similar size and shape as those found on cellular phones. In other embodiments, a nickel-cadmium ("NiCd"), nickel-metal hydride ("NiMH"), or alkaline (e.g., AA) batteries are used. A lithium-ion battery 700 is preferred because lithium-ion technology offers better battery runtime (e.g., approximately 14 hours), charge retention, and cycle life (e.g., approximately 1,000 charging cycles) than other battery technologies.

In some embodiments, the gas detector 10 includes a diagnostic port 550. The diagnostic port 550 may include a Universal Serial Bus ("USB") socket into which a USB cable can be inserted to allow the gas detector 10 to communicate with devices such as external devices 50. The USB connector 550 also allows the gas detector 10 to be field-programmable, that is, the gas detector 10 can be reconfigured, modified, or upgraded via the diagnostic 550. In some embodiments, the diagnostic port 550 also functions as a charging port for providing a charging current to the battery 700.

The sensors 110 through 140 that measure and detect hazardous gases, thus providing gas data to the processing unit 200, may require filter cartridges, calibration, and maintenance. A personal skilled in the art would have sufficient knowledge to understand the placement of such filter cartridges, performance of calibration, and maintenance of sensors 110 through 140 within the gas detector 10 as shown in FIG. 2.

Figure 3:
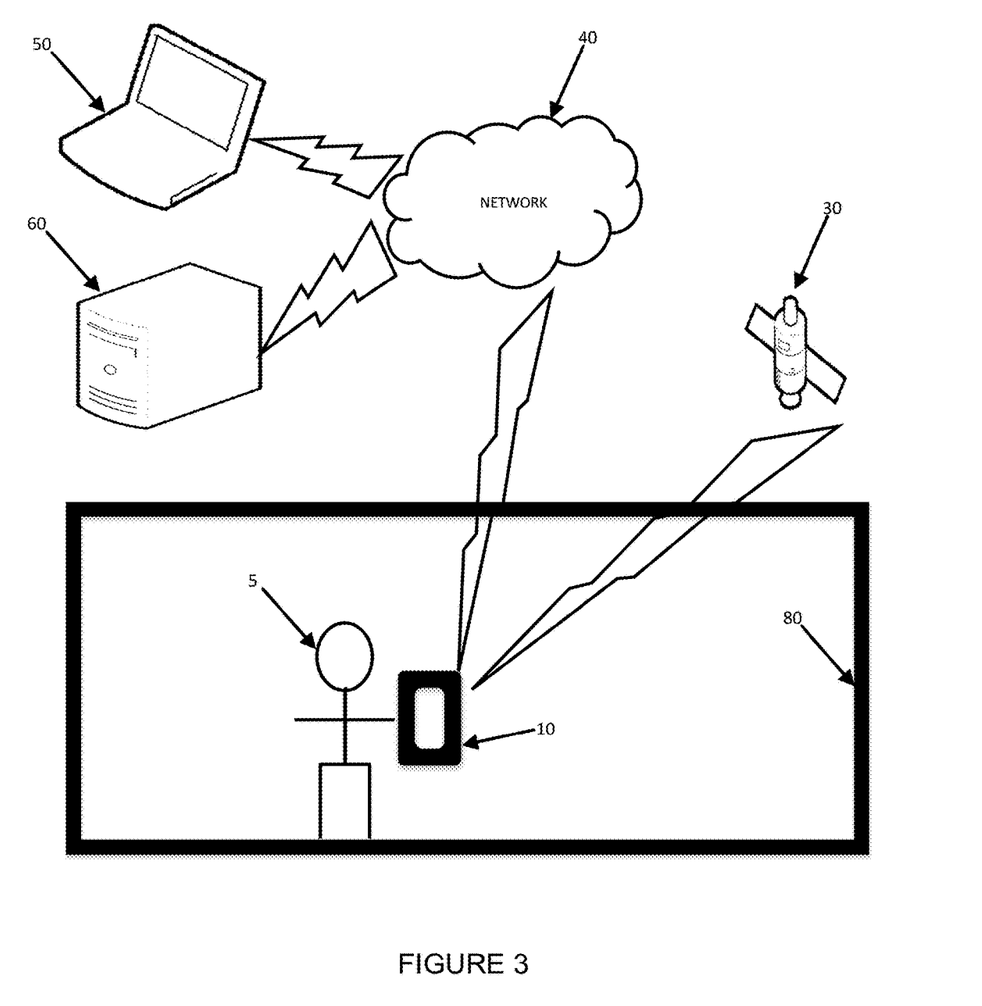
FIG. 3 illustrates a system overview of the gas detector, in accordance with the principles of the present invention.

FIG. 3 illustrates a system overview of the gas detector 10 used within a confined space 80, such as a room or environment, in accordance with an embodiment of the present invention. A user 5 carries and uses the gas detector 10 within the confined space 80. In some embodiments, a plurality of users 5 carries and uses a plurality of gas detectors 10 within at least one confined space 80 simultaneously. As described above with respect to FIG. 2, the laser 170 can measure dimensions including, for example, a diameter, width, length, height, circumference of the confined space 80. In some embodiments, the dimensions (i.e., geometry data) determined (i.e., calculated) by the laser 170 (and other geometric sensors, for example, the level 180) can be used to calculate space data (more detail in reference to FIG. 5).

In some embodiments, the gas detector 10 communicates with a GPS satellite 30 via the location module 300. The GPS satellite provides the location module 300 with location data such as latitude, longitude, heading, time, and a GPS quality value.

The gas detector 10 communicates with a network 40 via the communication module 400. The network 40 may be a wireless personal-area-network such as Bluetooth, a wireless wide-area-network such as internet, or a Global Systems for Mobile Communications ("GSM") network. The communication module 400 is operable to transmit and receive signals via the network 40.

In some embodiments, a remote server 60 runs an application that wirelessly communicates with the gas detector 10 via the network 40. The remote server 60 may be configured to store logs of the events detected by the gas detector 10. In one embodiment, the processing unit 200 of the gas detector calculates space data based on the gas data, the geometry data, and the location data; in another embodiment, the remote server 60 calculates the space data based on the gas data, the geometry data, and the location data received from the gas detector 10 via the network 40. The space data can be, for example, a volume of the confined space 80, a distance to an exit of the confined space 80, etc. (more detail in reference to FIG. 5).

For example, the remote server 60 can be configured to provide a graphical user interface ("GUI") that users 5 can access using a computing device (e.g., a desktop computer, a laptop computer, a tablet computer, a smart phone, a smart watch, etc.). The GUI provided by the remote server 60 allows users 5 to view logs collected by a plurality of gas detectors 10, parameters calculated by the remote server 60, and alarms generated by the plurality of gas detectors 10.

Referring to FIG. 3, an external device 50 can connect to the network 40. The external device 50 (e.g., a cellular phone, personal computer, tablet, etc.) can receive the gas data, the geometry data, and/or the location data from the gas detector 10 via the network 40. In some embodiments, the gas detector 10 communications to the external device 50 via a Bluetooth connection and the external device communicates to a remote server 60 via a GSM network 40 to pass data between the gas detector and the remote server 60.

FIG. 4 illustrates the gas detector 10 in a block diagram format, in accordance with an embodiment of the present invention. A processing unit 200, a sensor module 100, a location module 300, a communication module 400, a user interface 500, a memory module 600, are connected by one or more control and/or data buses (labeled "DATA"). The control and/or data buses are shown generally in FIG. 4 for illustrative purposes. The use of one or more control and/or data buses for the interconnection between and communication among the various modules and components would be known to a person skilled in the art in view of the present invention described herein.

The sensor module 100 includes various sensors that have been previously described with respect to FIGS. 1 and 2. For subsequent disclosure, the LEL sensor 110, the oxygen sensor 120, the first toxic sensor 130, and the second toxic sensor 140 have been referred to as a plurality of gas sensors (e.g., providing gas data). In some embodiments, the plurality of gas sensors includes the temperature sensor 150 and the humidity sensor 160.

For subsequent disclosure, the laser 170 and the level 180 have been referred to as at least one geometry sensor (e.g., providing geometry data). In addition, data received and generated by the location module 300 has been referred to as location data in the subsequent disclosure.

The processing unit 200 can be comprised of one or more processors. For example, the processing unit 200 can be comprised of a "normal operation" processor and an "alarm" processor; the alarm processor controls operation of the gas detector 10 when the gas data is above a threshold (more detail in FIG. 5). Data, such as gas, geometry and/or location, received and calculated by the processing unit 200 is stored in the memory module 600. The user 5 can view and manipulate data via the user interface 500, comprised of, for example, the displays 510 and 520 (i.e., LCD display screen and LED alarm bar), the audible speaker 530, the plurality of buttons 540, and the diagnostic port 550.

The communication module 400 of the gas detector 10 includes, for example, the Bluetooth chip 410, the GSM chip 420, and the antenna 430. In some embodiments, more than one antenna 430 can be present, for example, but not limited to, a first antenna for GSM communication and a second antenna for GPS satellite communication.

Power is delivered to components of the gas detector 10 from the battery 700 over one or more power buses (labeled "POWER"). The power buses are shown generally in FIG. 4 for illustrative purposes. In some embodiments, power from the battery 700 can be conserved by placing one or more sensors of the sensor module 100 in a sleep more and/or changing the frequency at which gas data, geometry data, and/or location data is detected and measured.

Figure 5:
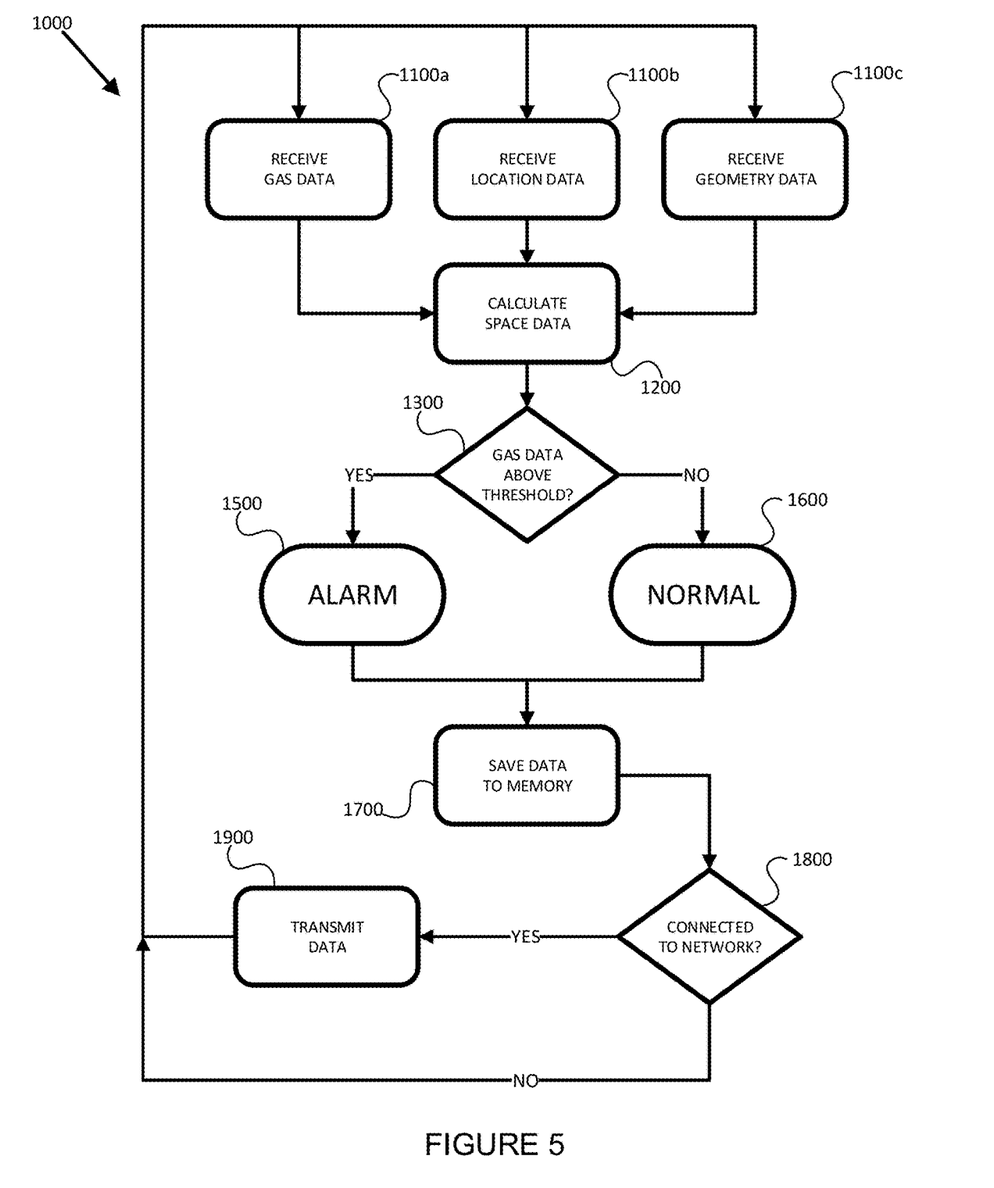
FIG. 5 illustrates a flowchart of a process for monitoring gas, in accordance with the principles of the present invention.

FIG. 5 illustrates a flowchart of a process 1000 for monitoring gas, in accordance and embodiment of the present invention. The process 1000 is associated with and described herein with respect to the gas detector 10 used in the confined space 80. Various steps described herein with respect to the process 1000 are capable of being executed simultaneously, in parallel, or in an order that differs from the illustrated serial manner of execution. The process 1000 is also each capable of being executed using fewer steps than are shown in the illustrated embodiment. For example, one or more functions, formulas, or algorithms can be used to calculate space data based on the gas data and the geometry data and/or determine whether gas data is above a threshold.

The process 100 for monitoring gas includes receiving gas data from a plurality of gas sensors including, but not limited to, an LEL sensor 110, oxygen sensor 120, first toxic sensor 130, second toxic sensor 140 at step 1100a. The processing unit 200 receives a current indicative of the gas data. In some embodiments, the processing unit 200 transfers the gas data to the display 510 for the user 5 to view. At step 1100b, the processing unit 200 receives location data (e.g., GPS data) from the GPS satellite via the location module 300.

At step 1100c, the processing unit 200 receives geometry data from the at least one geometry sensor (i.e., the laser 170, the level 180, etc.). The geometry data can be, for example, a distance calculated by the laser 170. In some embodiments, the distance is indicative of a dimension of the confined space 80 (e.g., a width, a length, a diameter, a circumference, etc.). In other embodiments, more than one dimension of the confined space 80 is measured by the at least one geometry sensor.

The processing unit 200 calculates space data at step 1200, based on the gas data, the location data, and/or the geometry data. The space data is related to a characteristic of the confined space 80. In one embodiment, the space data is calculated (i.e., determined) from the geometry data, such as a volume of the confined space, a surface area of the confined space 80, the size of an exit from the confined space 80, etc. In another embodiment, the space data is calculated or determined from the gas data and the geometry data, such as a volume of a hazardous gas in the confined space (calculated as a percentage volume of the gas multiplied by the volume of the confined space 80), the estimated amount of time for the hazardous gas to disperse and/or empty from the confined space 80 which can be calculated using additional information about estimated flow rates of gases within the confined space 80. In yet another embodiment, the space data is calculated or determined from the gas data and the location data, such as a distance from the present location of the gas detector 10 to an exit of the confined space 80, a distance between at least two gas detectors 10, for example.

If the gas data (e.g., a measured hazardous gas level) is above a threshold at step 1300, the processing unit 200 initiates an "ALARM" state of operation (step 1500). Otherwise, if the gas data is equal to or below the threshold at step 1300, the processing unit 200 continues in a "NORMAL" state of operation (step 1600). The threshold is, for example, a concentration of gas that is hazardous to users 5, represented as a percentage of volume of a particular gas, such as, for example, carbon monoxide, hydrogen sulfide and/or an amount of gas particles, including, for example, ammonia, and VOC, that is hazardous to users 5, represented as a count (e.g., parts per million) of a particular gas.

During the "ALARM" state of operation at step 1500, the processing unit 200 adjusts the interval of gas data collection by the plurality of gas sensors and/or location data collection by the location module 300. For example, the plurality of gas sensors can detect and measure gas data every half second during the "ALARM" state (compared to every five seconds during the "NORMAL" state). Additionally, the processing unit 200, at least one warning message is displayed on the display 510 and/or the LED bar 520 and an alarm sound is initiated through the audible speaker 530. In some embodiments, an alarm processor (i.e., a second processor) works alone or in combination with the processing unit 200 during the "ALARM" state.

During the "NORMAL" state of operation at step 1600, the processing unit 200 uses a preset interval of gas data collection by the plurality of gas sensors that is longer than the interval during the "ALARM" state (e.g., every five seconds). No visual or audible alarm is initiated.

At step 1700, the processing unit 200 stores the gas data, the location data, the geometry data, and/or the space data in the memory module 300 (e.g., a removable SD card). The memory module 300 is capable of saving several days of data for later retrieval.

The processing unit 200 determines whether the communication module 400 is connected to the network 40 at step 1800. If the communication module 400 is connected to the network 40, the gas detector 40 is able to transmit the gas data, the location data, the geometry data, and/or the space data to at least one of the external device 50 and the remote server 60. Otherwise, the data is not transmitted.

At step 1900, the communication module 400 transmits the data from the memory module 300 to at least one of the external device 50 and the remote server 60. In one embodiment, the Bluetooth chip 410 transmits the data over a Bluetooth connection 40. In another embodiment, the GSM chip 420 transmits the data over a GSM network 40, for example using antenna 430.

The process 1000 is repeated continuously during operation of the gas detector 10. The user 5 is able to adjust the interval of data collection and transmission using the plurality of buttons 540. For example, the user 5 can select an interval of detection and measurement of gas data by the plurality of gas sensors, such as, but not limited to, an LEL sensor 110, oxygen sensor 120, first toxic sensor 130, second toxic sensor 140, between half a second and several minutes (e.g., 5 minutes, 30 minutes, etc.).

Figure 6:
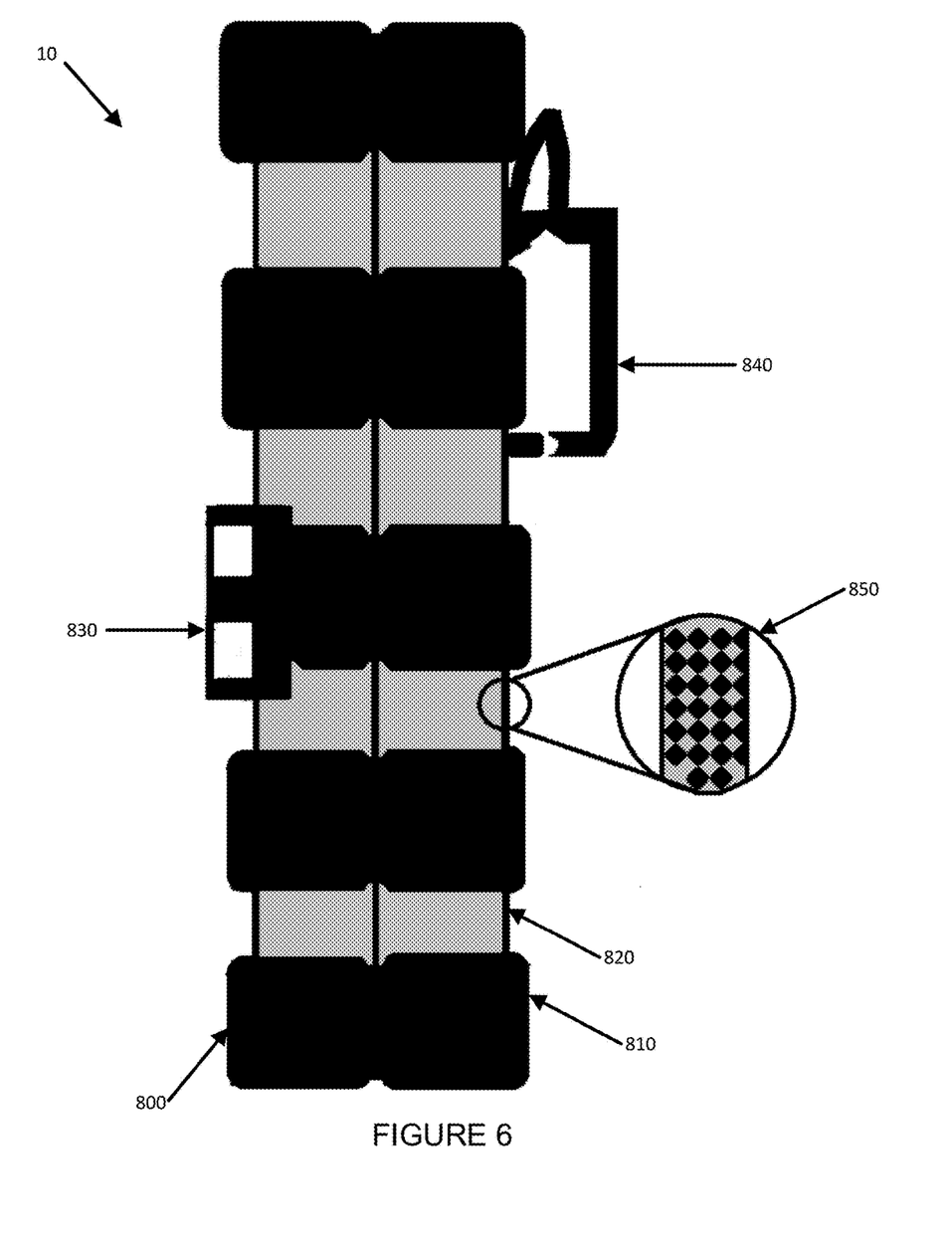
FIG. 6 illustrates a side view of the gas detector, in accordance with the principles of the present invention.

FIG. 6 illustrates a side view of the gas detector 10, in accordance with an embodiment of the present invention. The gas detector 10 includes an enclosure 800. As described above with respect to FIG. 1, the enclosure 800 protects internal components of the gas detector 10 from dirt and water (i.e., the environment). A clasp 830 allows access to internal (e.g., electronic) components of the gas detector 10. The enclosure 800 may provide ingress protection rated at IP-65 or IP-67.

In some embodiments, the enclosure 800 includes a first type of rubber 810 and a second type of rubber 820. The first type of rubber 810 can be, for example, vulcanized (i.e., hard) rubber and the second type of rubber 820 can be, for example, soft rubber, for instance, but not limited to, natural rubber, silicone rubber, butyl rubber, etc.). The combination of the first type of rubber 810 and the second type of rubber 820 provides shock absorption and drop protection for the gas detector 10. Additionally, the second type of rubber 820 may include a honeycomb design 850, for example a waffle design. The honeycomb design 850 provides a larger surface area soft rubber 820, which provides further shock absorption for internal components of the gas detector 10.

The enclosure 800 may include a viewing port (not shown) overlapping the display 510. The viewing port can be made from, for example, clear plastic, strengthened glass, treated glass, or synthetic sapphire sheet. Synthetic sapphire sheets are difficult to scratch and extremely resistant to corrosion.

Referring to FIG. 6, the enclosure 810 may include a clamp mechanism 840 (e.g., an alligator clip). The clamp mechanism 840 allows the gas detector 10 to be attached to the user 5. With the gas detector 10 attached to the user 5 (e.g., at the clothing), the user 5 can perform work while still detecting and measuring hazardous gases in the confined space.

As to the manner of usage and operation of the present invention, the same should be apparent from the above description. Accordingly, no further discussion relating to the manner of usage and operation will be provided.

While an embodiment of the gas detector has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described, and that each embodiment is also provided with features that may be applicable to other embodiments. It is to be understood that the invention includes all such variations and modifications that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A gas detector for use in a confined space, the gas detector comprising:
   a plurality of gas sensors operable to measure one or more hazardous materials;
   a location module;
   at least one geometry sensor;
   a communication module; and
   a processor configured to
      receive gas data from the plurality of gas sensors,
      receive location data from the location module,
      receive geometry data from the at least one geometry sensor, calculate space data based on at least one of the gas data and the geometry data, wherein the space data is a characteristic of the confined space, and transmit a signal based on at least two selected from the group consisting of the gas data, the location data, and the space data using the communication module.

2. The gas detector of claim 1, wherein the plurality of gas sensors consists of a lower explosive limit ("LEL") sensor, an oxygen sensor, a first toxic sensor, and a second toxic sensor.

3. The gas detector of claim 2, wherein the LEL sensor is an infrared sensor and the oxygen sensor is a lead-free sensor.

4. The gas detector of claim 1, wherein the at least one geometry sensor is selected from the group consisting of a laser and a level.

5. The gas detector of claim 4, wherein the geometry data consists of a distance.

6. The gas detector of claim 1, wherein the processor is further configured to store at least one of the gas data, the location data, geometry data, and the space data in a memory module.

7. The gas detector of claim 1, further comprising a graphical user interface and an audible speaker.

8. The gas detector of claim 7, wherein the processor compares the gas data to a threshold and, when the gas data is above the threshold, performs an operation selected from the group consisting of displaying a warning message on the graphical user interface and sounding a warning sound through the audible speaker.

9. The gas detector of claim 1, wherein the signal transmitted to at least one of an external device and a remote server using communication module.

10. The gas detector of claim 1, further comprising an enclosure composed of a first type of rubber and a second type of rubber, wherein the enclosure further consists of a clamp mechanism and a honeycomb design.

11. The gas detector of claim 1, wherein the space data consists of at least one of a volume of the confined space and a distance to an exit of the confined space.

12. The gas detector of claim 1, wherein the space data is calculated based on both of the gas data and the geometry data.

13. The gas detector of claim 12, wherein the space data consists of at least one of a volume of the gas and an estimated time for the hazardous gas to disperse from the confined space.

14. A method for monitoring gas in a confined space, the method comprising:

detecting, using a plurality of gas sensors, gas data based on one or more hazardous materials in a confined space;

receiving, using a location module, location data;

detecting, using at least one geometry sensor, geometry data of the confined space;

calculating, using a processor, space data based on the gas data and the geometry data, wherein the space data is a characteristic of the confined space; and transmitting, using a communication module, a signal based on at least two selected from the group consisting of the gas data, the location data, the geometry data, and the space data.

15. The method of claim 14, wherein the geometry data consists of a distance.

16. The method of claim 15, wherein the space data consists of at least one of a volume of the confined space and a distance to an exit of the confined space.

17. The method of claim 15, wherein the space data is calculated based on both of the gas data and the geometry data.

18. The method of claim 17, wherein the space data consists of at least one of a volume of the gas and an estimated time for the hazardous gas to disperse from the confined space.

19. The method of claim 14, further comprising comparing, at the processor, the gas data to a threshold, displaying, on a graphical user interface, a warning message on the graphical user interface when the gas data is above the threshold, and sounding, through an audible speaker, a warning sound when the gas data is above the threshold.

20. The method of claim 14, further comprising storing, in a memory module, the gas data, the location data, the geometry data, and the space data.

* * * * *